US008484768B2

(12) United States Patent
Leatt et al.

(10) Patent No.: US 8,484,768 B2
(45) Date of Patent: Jul. 16, 2013

(54) NECK BRACE (75) Inventors: Christopher J. Leatt, Constantia (ZA); MarK E. Hopkins, Cape Town (ZA); Grant L. Nelson, Cape Town (ZA)

(73) Assignee: Xceed Holdings CC, Durbanville (ZA)

( * ) Notice: Subject to any disclaimer, the term of this patent is extended or adjusted under 35 U.S.C. 154(b) by 697 days.

(21) Appl. No.: 12/447,452

(22) PCT Filed: Oct. 26, 2007

(86) PCT No.: PCT/IB2007/054363
§ 371 (c)(1),
(2), (4) Date: Dec. 23, 2009

(87) PCT Pub. No.: WO2008/050307
PCT Pub. Date: May 2, 2008

(65) Prior Publication Data
US 2010/0088809 A1    Apr. 15, 2010

(30) Foreign Application Priority Data

Nov. 26, 2003 (ZA) .................................. 2003/9174
Oct. 26, 2006 (ZA) .................................. 2006/08900

(51) Int. Cl.
*A41D 13/00* (2006.01)
(52) U.S. Cl.
USPC ..................................... 2/468; 2/421; 602/18
(58) Field of Classification Search
USPC .................... 2/410, 468, 415, 422; 602/17–19
See application file for complete search history.

(56) References Cited

U.S. PATENT DOCUMENTS

| 3,134,106 | A | * | 5/1964 | Shaffer et al. ..................... 2/462 |
| 3,189,917 | A | * | 6/1965 | Sims ................................. 2/415 |
| 3,285,243 | A | * | 11/1966 | Yellin ............................. 602/18 |
| 3,514,784 | A | * | 6/1970 | McDavid .......................... 2/468 |
| 3,601,123 | A | * | 8/1971 | McFarland ...................... 602/18 |

(Continued)

FOREIGN PATENT DOCUMENTS

| SI | 9600306 | 4/1998 |
| WO | 9938401 | 8/1999 |

(Continued)

OTHER PUBLICATIONS

International Search Report. PCT/IB2007/054363. Mailed Mar. 25, 2008.

*Primary Examiner* — Richale Quinn
(74) *Attorney, Agent, or Firm* — Novak Druce Connolly Bove + Quigg LLP (57) ABSTRACT

A neck brace (10) comprises an impact surface (39,55) adjacent the neck of a wearer of the brace (10) that it is spaced from a helmet (42) and that is configured to limit movement of the helmet by contacting an underside (46) of the helmet, a bearing surface (15,35) bearing on the wearer's body; and a resilient structure (12) between the impact surface (39,55) and the bearing surface (15,35) for transferring impact loads from the helmet (42) on the impact surface, to the wearer's body via the bearing surface. The brace (10) further includes restraining means (58) that is attachable to the rear of the structure (12) with a releasable clip mechanism (66) and to the helmet (42) to inhibit movement of the helmet. The restraining means is in the form of a tether (58) that is attached to the helmet (42) at two spaced locations and that passes with clearance through an aperture in an anchor element (62,64), to allow the helmet (42) to be moved freely while the tether (58) slides through the aperture.

18 Claims, 5 Drawing Sheets

U.S. PATENT DOCUMENTS

| | | | |
|---|---|---|---|
| 3,671,974 A * | 6/1972 | Sims | 2/421 |
| 3,818,509 A * | 6/1974 | Romo et al. | 2/421 |
| 4,290,150 A * | 9/1981 | Guerre-Berthelot | 2/421 |
| 4,324,003 A * | 4/1982 | Johnston | 2/468 |
| 4,598,430 A * | 7/1986 | Nava | 2/410 |
| 4,638,510 A * | 1/1987 | Hubbard | 2/6.1 |
| 4,807,605 A * | 2/1989 | Mattingly | 602/19 |
| 4,827,915 A * | 5/1989 | Gorsen | 602/18 |
| 4,881,529 A * | 11/1989 | Santos | 2/468 |
| 5,230,698 A * | 7/1993 | Garth | 602/18 |
| 5,272,770 A * | 12/1993 | Allen et al. | 2/421 |
| 5,404,590 A * | 4/1995 | Monica, Jr. | 2/468 |
| 5,517,699 A * | 5/1996 | Abraham, II | 2/425 |
| 5,546,601 A * | 8/1996 | Abeyta | 2/468 |
| 5,546,609 A * | 8/1996 | Rush, III | 2/413 |
| 5,893,174 A * | 4/1999 | Primeau | 2/424 |
| 6,163,891 A * | 12/2000 | Viitalahti | 2/422 |
| 6,872,188 B2 * | 3/2005 | Caille et al. | 602/18 |
| 6,874,170 B1 * | 4/2005 | Aaron | 2/468 |
| 7,141,031 B2 * | 11/2006 | Garth et al. | 602/18 |
| 7,846,117 B2 * | 12/2010 | Leatt et al. | 602/18 |
| 7,993,293 B2 * | 8/2011 | Leatt | 602/18 |
| 8,002,723 B2 * | 8/2011 | Leatt | 602/18 |
| 2003/0060744 A1 * | 3/2003 | Caille et al. | 602/18 |
| 2005/0206151 A1 * | 9/2005 | Ashline | 280/801.1 |
| 2008/0177209 A1 * | 7/2008 | Leatt et al. | 602/18 |
| 2010/0088809 A1 * | 4/2010 | Leatt et al. | 2/468 |

FOREIGN PATENT DOCUMENTS

| | | |
|---|---|---|
| WO | 02089620 | 11/2002 |
| WO | 2005051251 | 6/2005 |
| WO | WO 2005051251 A2 * | 6/2005 |

* cited by examiner

Figure 7

NECK BRACE

CROSS-REFERENCE TO RELATED APPLICATIONS

This application is a national stage application under 35 USC §371(c) of PCT Application No. PCT/IB2007/054363, entitled "Neck Brace," filed on Oct. 26, 2007, which claims priority from South African Patent Application No. 2006/08900, filed on Oct. 26, 2006. This application is a continuation-in-part of U.S. patent application Ser. No. 11/440,576, entitled "Neck Brace", filed on May 25, 2006, which is a continuation of International Application No. PCT/ZA2004/000148, entitled "Neck Brace", filed on Nov. 26, 2004, which claims priority form South African Patent Application No. 2003/9174, filed on Nov. 26, 2003. The entire disclosure and contents of the above applications are hereby incorporated by reference herein.

FIELD OF THE INVENTION

This invention relates to protective gear for preventing injury to the neck and upper cervical spine, when wearing a helmet. In particular, the invention relates to a neck brace.

BACKGROUND TO THE INVENTION

An earlier neck brace has been developed by one of the inventors of the present invention and is disclosed in International Patent Application No. PCT/ZA2004/000148, published as WO 2005/051251, the contents of which is included herein in its entirety, by reference. This earlier neck brace offers protection to the neck and upper cervical spine, when worn in conjunction with a helmet.

However, tests showed that the protection offered by this earlier neck brace during very rapid decelerations, such as those found in accidents during motor sports, the interaction between the lower parts of the helmet and the brace could still be improved. This was due to a number of reasons.

The first shortfall in the earlier brace was that the helmet and head were found to travel too far forward relative to the brace, causing the helmet to travel past the forward end of the brace and causing strain on the upper cervical spine as the helmet rotated forward.

The second shortfall in the earlier brace was that shoulder straps that were used to keep the brace in position on the wearer's chest, slid off the brace.

What complicates addressing these shortfalls, is that it is important for the sake of comfort (and accordingly for wearer compliance) to prevent restricting movement of the wearer's head as far as possible during normal use of the brace. Further, the helmet should be capable of being fitted after the brace, both for the sake of convenience in allowing a wearer to prepare his brace, seatbelts and the like before fitting his helmet and also because a brace that could fit snugly enough, would be difficult and/or cumbersome to put on at the same time as the helmet.

The present invention seeks to provide a neck brace that addresses these shortfalls and improves in a number of other respects on the prior neck brace of International Patent Application No. PCT/ZA2004/000148.

SUMMARY OF THE INVENTION

According to one aspect of the present invention, there is provided a neck brace comprising:

at least one impact surface adjacent the neck of a wearer of the brace and facing generally upwardly, such that it is spaced from a helmet when the neck brace is worn with a helmet, said impact surface being configured to limit movement of the helmet by contacting an underside of the helmet;

at least one bearing surface which is shaped and configured to bear on the wearer's body; and a structure that extends between the impact surface and the bearing surface, said structure being sufficiently resilient to transfer impact loads from the helmet on the impact surface, to the wearer's body via the bearing surface;

wherein the brace further includes restraining means that is attachable to the structure and to the helmet.

The restraining means may be attachable to the rear of the structure, e.g. by means of a releasable clip mechanism and may be in the form of at least one elongate flexible element, such as a strap or tether.

The restraining means may be attachable to the helmet in at least two spaced locations and may include an elongate element that extends between the spaced locations. The restraining means may further include an anchor element that is attachable to the structure and that defines an aperture, the elongate element passing through the aperture with clearance to allow the elongate element to slide through the aperture when the helmet is moved, so as to avoid unnecessary inhibition of the wearer's head movements.

The restraining means may be attachable to a chin strap of the helmet or may be attachable to the outside of the helmet.

The neck brace may includes at least one lateral protuberance extending from the structure and being configured to extend along the body, e.g. the shoulders and/or chest, of the wearer, so that it can extend underneath a body restraint, such as a seatbelt of the wearer. Each of the protuberances may define a generally planar surface on which an elongate element of the body restraint, i.e. the seatbelt, is receivable and each protuberance may include an upstanding end, remote from the structure.

The structure may be generally rigid, may be in the form of a ring that can extend around the wearer's neck and may include a column that is fixedly attached to the structure and that extends from the rear of the structure in a position corresponding with the upper spine of the wearer.

The neck brace may include a flange extending from the structure, with the impact surface being defined on the upper surface of the flange.

The neck brace may include at least one upstanding protuberance extending from the impact surface and the protuberance may be configured to prevent a helmet of the wearer from sliding over the impact surface.

The structure may include at least two parts and at least one releasable clip mechanism configured to attach the parts of the structure to one another, the clip mechanism including a protuberance defined on a first part of the structure and a recess that is complementally shaped to the protuberance, defined on a second part of the structure, the protuberance and recess being shaped to allow pivotal movement between the two parts, when the protuberance is received in the recess.

According to another aspect of the present invention there is provided a neck brace comprising:

at least one impact surface adjacent the neck of a wearer of the brace and facing generally upwardly, such that it is spaced from a helmet when the neck brace is worn with a helmet, said impact surface being configured to limit movement of the helmet by contacting an underside of the helmet;

at least one bearing surface which is shaped and configured to bear on the wearer's body; and a structure that extends between the impact surface and the bearing surface, said structure being sufficiently resilient to transfer impact loads from the helmet on the impact surface, to the wearer's body via the bearing surface;

wherein the structure includes at least two parts and at least one releasable clip mechanism configured to attach the parts of the structure to one another, said clip mechanism including a protuberance defined on a first part of the structure and a recess that is complementally shaped to the protuberance, defined on a second part of the structure, the protuberance and recess being shaped to allow pivotal movement between the two parts, when the protuberance is received in the recess.

The clip mechanism may include a spigot formation about which the second part of the structure can pivot relative to the first part, when the protuberance is received in the recess.

The clip mechanism may be configured to draw the spigot closer to the first part of the structure, to lock the two parts of the structure against pivotal movement.

BRIEF DESCRIPTION OF THE DRAWINGS

For a better understanding of the present invention, and to show how the same may be carried into effect, reference will now be made, by way of non-limiting example, to the accompanying drawings in which.

DETAILED DESCRIPTION OF THE DRAWINGS

Referring to FIGS. 1 to 6 the drawings, a first embodiment of a neck brace in accordance with the present invention is generally indicated by reference numeral 10.

The neck brace 10 includes a structure in the form of a rigid ring 12 that is configured to extend around the neck of a wearer and that has a column 14 that is fixedly attached to the ring and that is configured to extend downwardly from the rear of the ring, generally along the upper spine of the wearer and is relatively wide so that it can transfer compressive loads to the back of the wearer via the under-surface or back bearing surface 15 of the column, without causing excessive injury or discomfort.

The ring 12 includes a first or rear part 16 and a second or front part 18, which are releasably connectable together by two laterally positioned clip mechanisms 20. The two parts 16,18 are separate from each other, but can be clipped fixedly, as shown in the drawings, or can be part clipped, allowing pivotal movement between them. This allows either one of the clip mechanisms 20 to be released entirely and the other clip mechanism to be part clipped, so that the rear part 16 and front part 18 can pivot about the part clipped mechanism and the ring can be fitted around the wearer's neck or can be removed.

Figure 4:
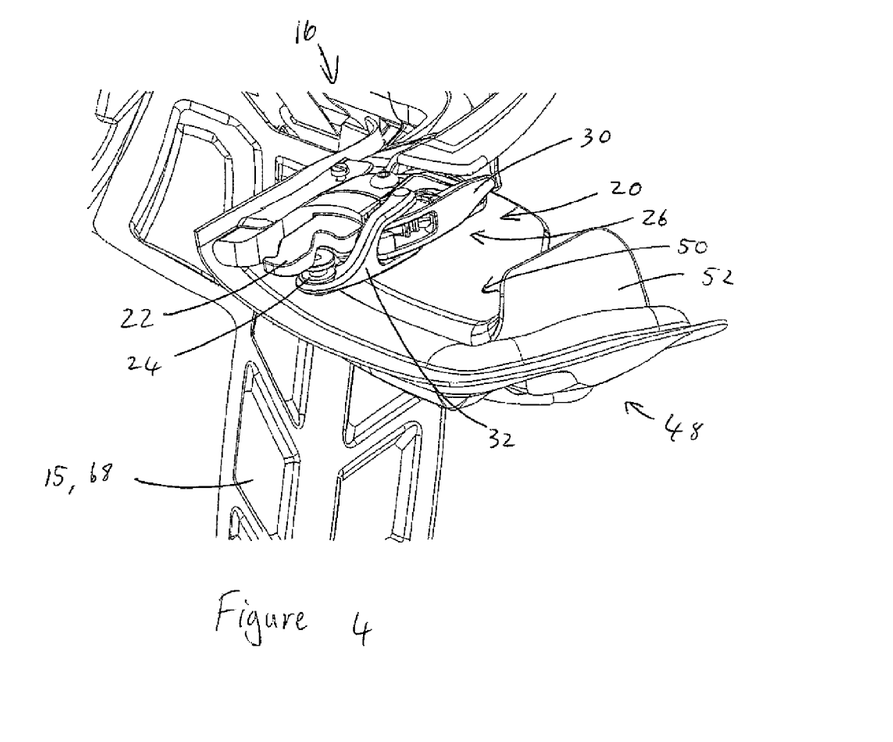
FIG. 4 is a detail view of part of a clip mechanism of the neck brace of FIG. 1.
Figure 5:
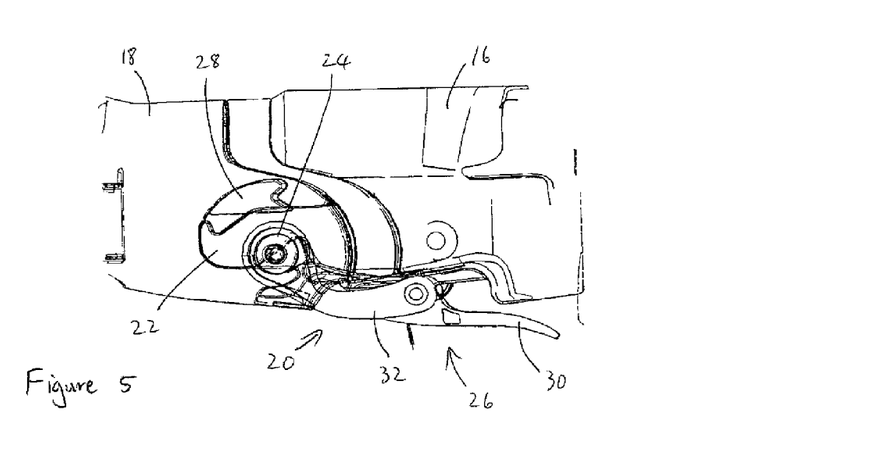
FIG. 5 is a sectional plan view through the clip mechanism, part of which is shown in FIG. 4.

Referring specifically to FIGS. 4 and 5, in the clip mechanism 20 on the wearer's left, the rear part 16 includes a protuberance 22. The clip mechanism 20 further includes a truncated spigot formation 24 and an over-centre mechanism 26 and is configured to draw the spigot rearward, when locked. On the front part 18, a recess 28 is defined that is complementally shaped to the protuberance 22 and that is internally recessed, so that the protuberance can rotate about the axis of the spigot 24, when inside the recess.

The clip mechanism 20 includes a lever 30 and a detent 32, on which the spigot 24 is formed. Both the lever 30 and detent 32 can be pivoted, to move the spigot 24 laterally outwardly and to withdraw it from an engagement which keeps the rear part 16 and front part 18 together. However, when the lever 30 is pivoted forward and the clip mechanism 20 is in its part clipped condition, the spigot 24 is still received in a complemental formation of the front part 18, so that the parts 16,18 cannot be separated, but there is a space between the parts, which allows pivotal movement as described above, about the spigot, while the protuberance 22 remains within the recess 28. To lock the parts 16,18 together, the lever 30 is pivoted rearward, which draws the detent 32 and spigot 24 rearward.

Figure 1:
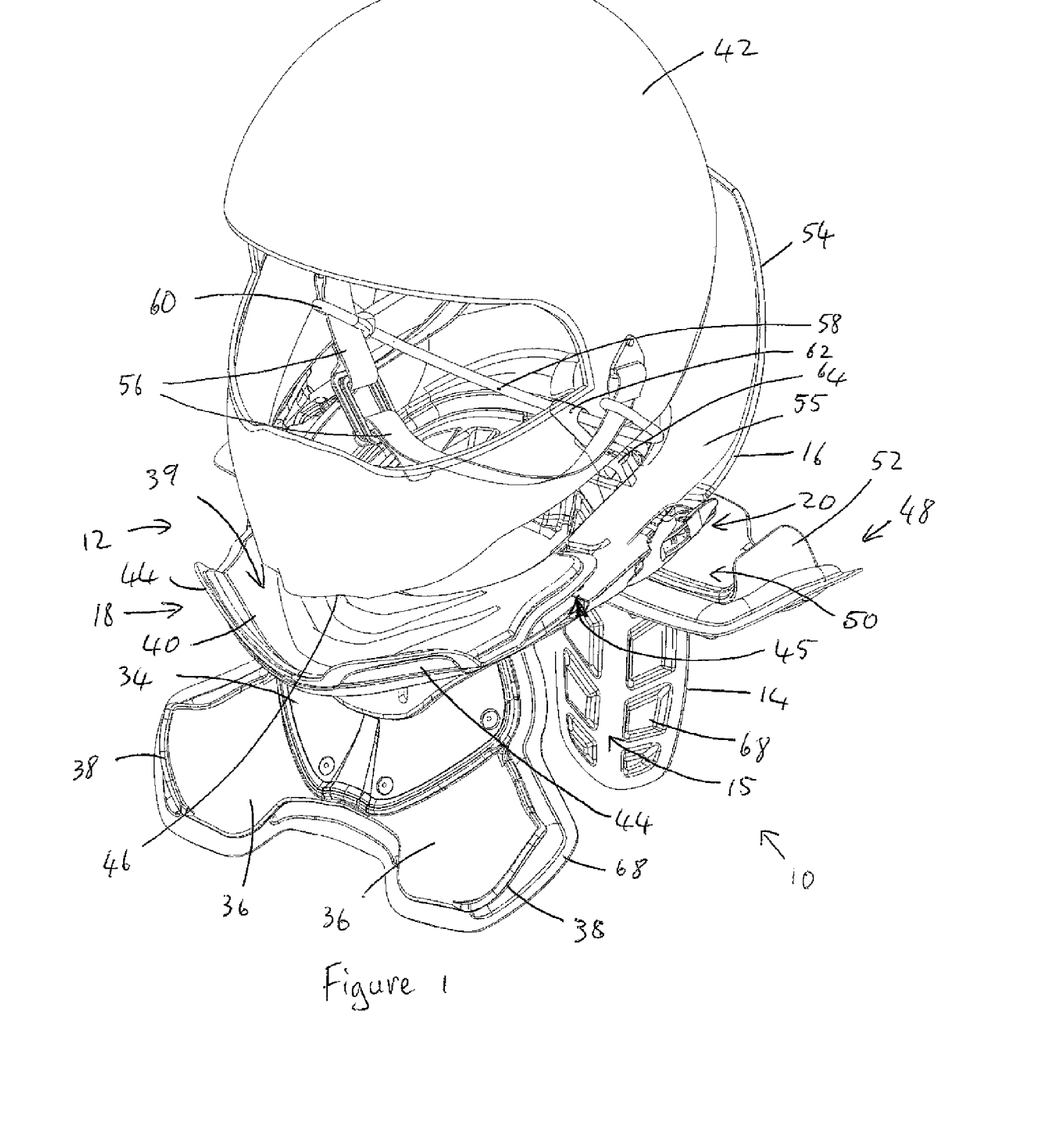
FIG. 1 is a three dimensional front view of a first embodiment of a neck brace in accordance with the present invention, and a helmet.
Figure 2:
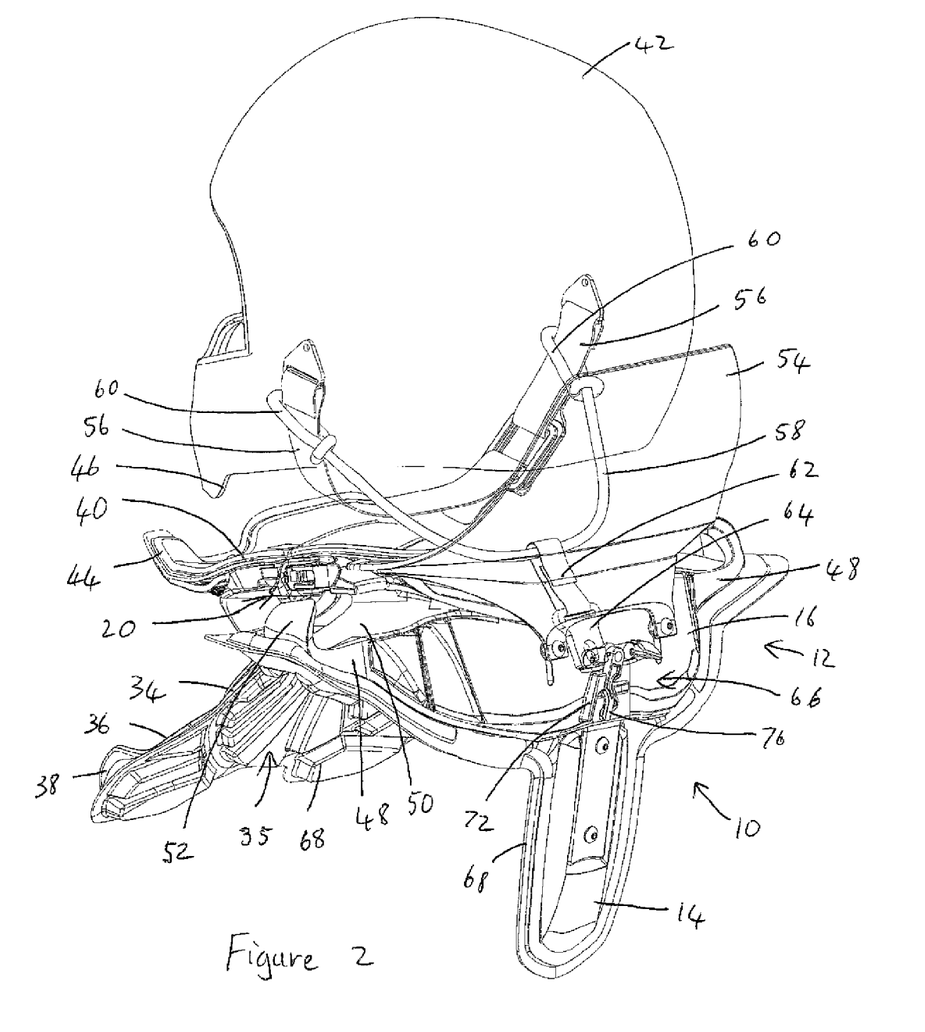
FIG. 2 is a three dimensional rear view of the neck brace and helmet of FIG. 1.
Figure 3:
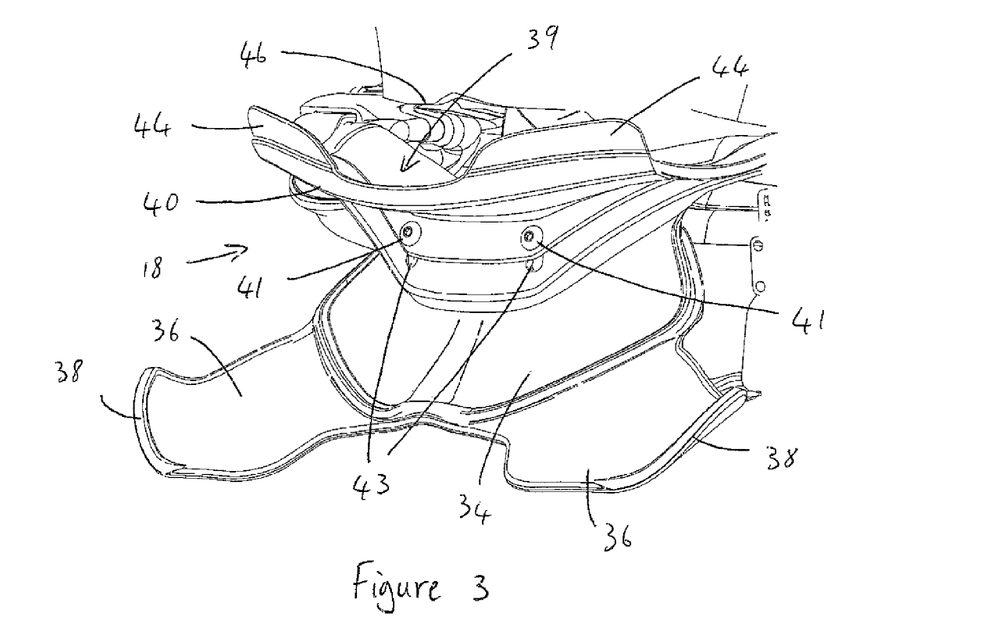
FIG. 3 is a detail three dimensional view of part of the neck brace of FIG. 1, taken form the front and slightly from below.

Referring to FIGS. 1 to 3, the ring 12 is shaped along its lower periphery so that an under-surface or bearing surface is defined that fits comfortably, yet snugly on the chest and shoulders of the wearer. In particular, the front part 18 includes a chest flange 34 with a chest bearing surface 35 underneath that is configured to fit snugly on the chest of the wearer and to transfer compressive loads from the ring 12 to the wearer's chest without causing excessive injury or discomfort.

Two lateral protuberances 36 are defined at the lower, outer corners of the chest flange 34, on which the straps of a seat harness or other body restraints of a wearer may press when the wearer is strapped into a seat of a vehicle. The remote ends 38 of these protuberances 36 stand slightly upwardly, to reduce the likelihood that such straps may slip off the protuberances.

Above the chest flange 34, the front part 18 includes a chin flange 40, that is spaced from the chest flange and that extends at a different angle, corresponding generally with the orientation of the underside of a full face helmet 42, worn by the wearer, in use. At the front edges of the chin flange, two upstanding protuberances in the form of ridges 44 are provided, at an obtuse angle relative to each other. The purpose of these ridges 44 is to prevent the front lower edge 46 of the helmet 42 from sliding forward past the ridges, as described below. The position of the chin flange 40 is adjustable, by adjusting capped screws 41 that can slide in slots 43, while rear ends of the chin flange are held captive in recesses 45, adjacent the clip mechanisms 20. The upper surface of the chin flange 40 forms an impact surface 39 on which the helmet 42 can impact, as will be described below.

The rear part 16 includes two lateral protuberances or anchors 48, each of which extends generally above the shoulders of the wearer and each of which defines a generally planar upper surface 50 and an upstanding end 52. In use, similarly to the protuberances 36, the anchors 48 are received underneath the straps of the wearer's body or seat restraints and the upstanding ends 52 prevent the straps from slipping off the anchors. The flat surfaces 50 are angled with the same orientation of the part of the seat restraints against which they typically press and experiments have shown that the anchors are less likely to slide relative to the straps in this configuration, than if their upper surfaces were rounded or at a different angular orientation.

The rear part 16 includes a protuberance or rear wall 54 that extends upwardly from its rear, against which the helmet 42 can press, in the event that the wearer's head is accelerated or rotated rearward, e.g. in the event of a rear impact during motor sport. The front surface of the rear wall 54 and the upper surface of the rear part 16 in front of the rear wall 54 form an impact surface 55 on which the helmet can impact.

Soft padding 68 is attached to the bearing surfaces 15 and 35, as well as all the other surfaces that face the wearer's body and that also perform the function of bearing surfaces.

The helmet 42 is attached to the head of the wearer in the conventional manner, by way of a releasable chin strap 56 with ends that are fixedly attached to the inside of the helmet's shell. The neck brace 10 includes restraining means in the form of an elongate, flexible element in the form of a restraining strap or tether 58 that is attachable to the neck brace and to the helmet 42.

The tether 58 is made of a material with very high tensile strength and forms a loop 60 at each of its ends. The loops 60 extend around chin strap 56 at two spaced locations adjacent the chin strap's respective attachments to the shell of the helmet 42 and this attachment allows the tether 58 to be attached to the chin straps of most conventional helmets.

At its rear, the part of the tether 58 between the loops 60 is received in a restraining loop 62 also of a material with high tensile strength and that fits loosely around the tether, to allow the tether to pass freely through the loop 62, when the wearer rotates his head sideways while wearing the helmet 42. At its lower end, the loop 62 is attached to a buckle 64 that is receivable in a releasable clip mechanism 66 in the rear part 16 of the ring 12, the loop 62 and buckle 64 forming an anchor element of the attachment means. The clip mechanism 66 is configured to receive the buckle 64 immediately in front of the base of the rear wall 54.

The tether 58 and loop 62 remain attached to the helmet 42 via its chin strap 56, when not in use. In use, the wearer fits the neck brace 10 around his neck and shoulders and passes the straps of his seat restraints over the protuberances 36 and anchors 48 as described herein above. The wearer then puts on the helmet 42 in the conventional way, presses the buckle 64 into the clip mechanism 66 and locks it in position, possibly by way of a clipping action, but preferably in a way that requires positive action from the wearer.

During normal use of the neck brace 10 and helmet 42, the lower edge 46 of the helmet is spaced from the impact surfaces 39,55 ring 12 and the tether 58 passes freely through the loop 62, so that typical movement of the wearer's head is not restrained excessively.

In the event of a front impact or other incident that causes rapid deceleration, the momentum of the wearer's head would tend to move it forward and to rotate forward about the upper cervical spine. This rotation should preferably be allowed to take place only to a limited extent and excessive rotation is inhibited by the front lower edge 46 of the helmet being rotated until it contacts the impact surface 39 of the chin flange 40 and cannot rotate further.

In the event of extremely rapid decelerations, the edge 46 may tend to slide forward on the chin flange 40, but it is prevented from sliding off the chin flange by the ridges 44. The orientation of the ridges 44 at an obtuse angle causes them to act in a funnelling manner, urging the chin bar of the helmet to slide to a centrally aligned orientation in the event that the wearer's head is turned sideways at the moment of impact.

As mentioned above, during rapid deceleration, the head and helmet 42 tends to rotate forward. This rotation is even more severe in cases where the front lower edge 46 presses against the ridges 44, which act as a fulcrum about which the helmet tends to rotate. The rotation of the helmet 42 could cause very severe injury to the upper cervical spine of the wearer, but this is ameliorated in the present invention by the tether 58, which is placed under tension by the initial rotation of the helmet and head and which then prevents further rotation by restraining the helmet from moving further away from the back of the ring 12, where the strap is attached by way of the loop 62, buckle 64 and clip mechanism 66.

During the deceleration, the chin strap 56 is also placed under tension by the rotation of the helmet and the attachment of the tether 58 to the chin strap causes the tension of either of these two tensile elements to be transferred to the other, thus enhancing the restraining action of both tensile elements.

When the wearer wants to remove the helmet 42, the buckle 64 is withdrawn from the clip mechanism 66, so that the helmet can be removed, with the tether 58, loop 62 and buckle still attached to it.

Figure 6:
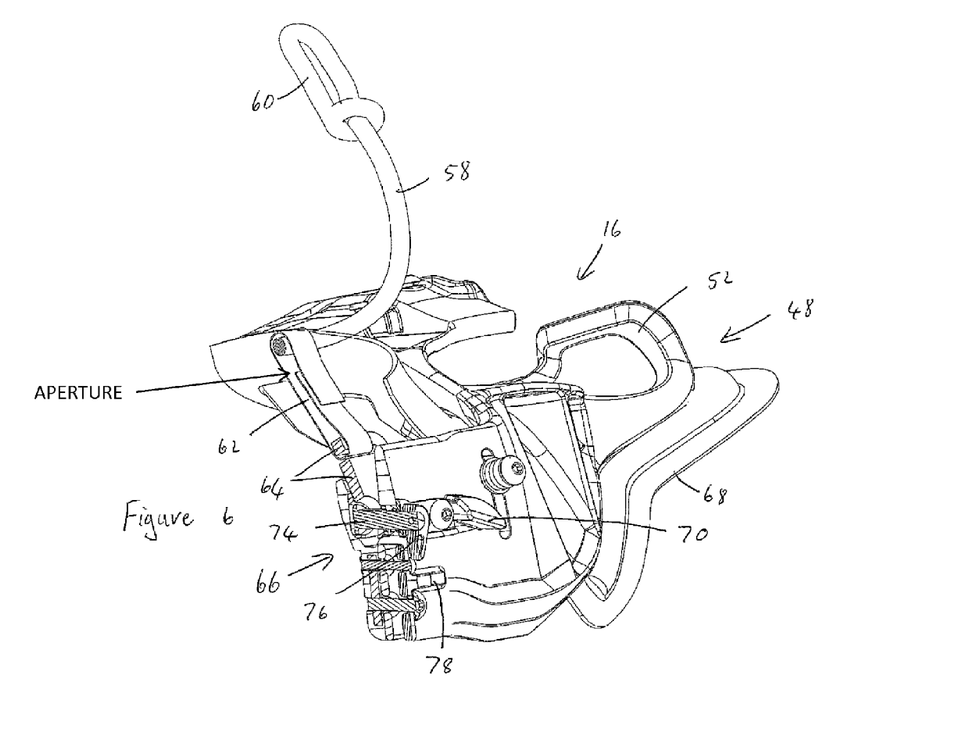
FIG. 6 is a sectional view of a rear part of the neck brace of FIG. 1.

The clip mechanism 66 is in the form of a quick release mechanism, details of which are best illustrated in FIG. 6. The clip mechanism 66 includes a non-round internal pin 74 over which the buckle 64 can pass only when the pin is in a specific orientation. At the rear of the pin, there is a quick release lever 76, that is connected to the pin and that can be used to rotate the pin. When the lever 76 is in a generally vertical orientation, as shown in the drawings, the pin 74 is in an orientation in which the buckle 64 cannot slide off the pin and is thus held captive within the clip mechanism 66. When the lever 76 is pivoted to a horizontal orientation, the pin 74 has an orientation that allows the buckle 64 to be withdrawn from the mechanism 66 and for the helmet to be removed form the neck brace and thus from the wearer's head.

Two stop formations 70 and 72 are provided to limit the pivotal movement of the lever 76 between its generally horizontal orientation in which the clip mechanism 66 is released and its generally vertical orientation in which the clip mechanism is locked. A ramped clip 78 is provided, with a sloping surface along which the lever 76 can slide when pivoted from its horizontal orientation towards its vertical orientation and which defines a gap between the clip 78 and the stop formation 70 in which the lever can be held captive in its vertical orientation by way of a clipping action. The buckle 64 can thus only be locked into the clip mechanism 66 if a user pivots the lever 76 to its vertical orientation, thus requiring positive action from the user. During use, the lever 76 remains in its vertical orientation, held captive by the clip 78. However, if the buckle 64 needs to be released, e.g. when the helmet is to be removed, this can be done very easily by pivoting the lever 76 out off the gap between the clip 78 and strop formation 70 towards its horizontal orientation. This can typically be done in a single movement.

In another embodiment of the invention that is not illustrated, the neck brace 10 can include a remote operation mechanism that allows the clip mechanism 66 or quick release mechanism 70 to be released from a remote location, e.g. from the side of the neck brace, by way of a cable, rod, or the like, extending to the mechanism.

Figure 7:
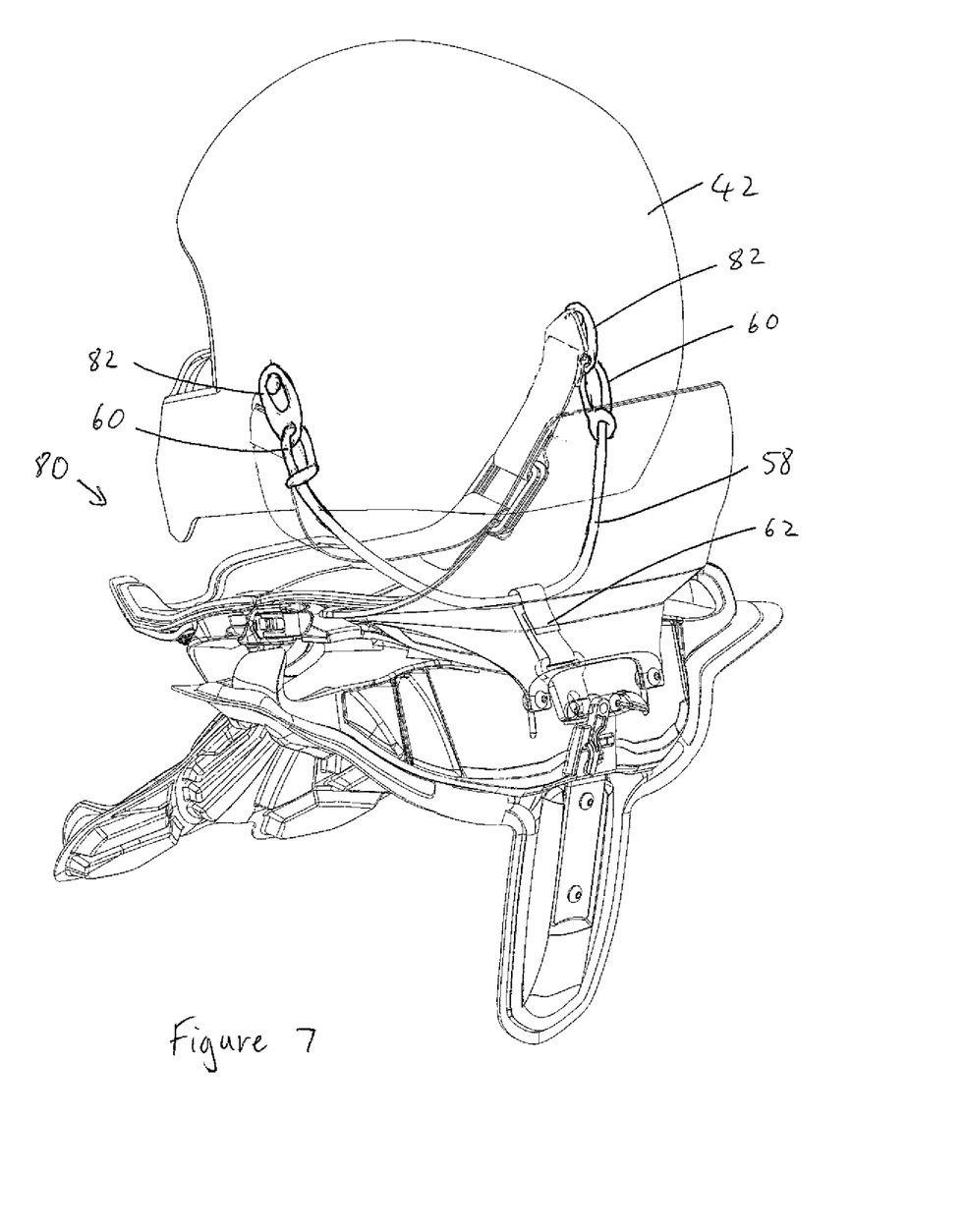
FIG. 7 is a three dimensional rear view of a second embodiment of a neck brace in accordance with the present invention, and a helmet.

Referring to FIG. 7, a second embodiment of a neck brace in accordance with the present invention is generally indicated by reference numeral 80 and is identical to the neck brace 10 shown in FIGS. 1 to 7, except that the loops 60 its tether 58 is attached to the outside of the helmet 42 by way of clips 82. The clips 82 can be releasable to allow the helmet to be removed from the wearer's head while still wearing the neck brace 80, i.e. the release of the clips 82 can serve as a back for the clip mechanism 66. This embodiment of the invention offers a significant advantage over existing systems with restraining tethers attached to helmets, in that the sliding of the tether 58 through the loop 62 allows the helmet 42 and thus the wearer's head to be rotated with much more freedom.

The invention claimed is:

1. A neck brace comprising:
   at least one impact surface adjacent the neck of a wearer of the brace and facing generally upwardly, such that it is spaced from a helmet when the neck brace is worn with a helmet, said impact surface being configured to limit movement of the helmet by contacting an underside of the helmet;
   at least one bearing surface which is shaped and configured to bear on the wearer's body; and
   a structure that extends between the impact surface and the bearing surface, said structure being sufficiently resilient to transfer impact loads from the helmet on the impact surface, to the wearer's body via the bearing surface, wherein the structure includes at least two parts and at least one releasable clip mechanism configured to attach the parts of the structure to one another, said clip mechanism including:
   (a) a protuberance defined on a first of the at least two parts of the structure;
   (b) a recess that is complementally shaped to the protuberance, defined in a second of the at least two parts of the structure, the protuberance and recess being shaped to allow pivotal movement between the protuberance and recess, relative to an axis within the clip mechanism, when the protuberance is received in the recess; and
   (c) a spigot about which the second part of the structure can pivot relative to the first part, when the protuberance is received in the recess, wherein said axis within the clip mechanism about which the protuberance and recess can pivot relative to each other when the protuberance is received inside the recess, is the axis of the spigot.

2. The neck brace of claim 1, wherein the clip mechanism includes a detent that is configured to pivot about the axis of the spigot to draw the spigot closer to the first part of the structure, and to hold the two parts of the structure together and to hold the protuberance inside the recess.

3. The neck brace of claim 2, wherein the clip mechanism includes a lever that can pivot to lock the detent in its clipped condition and to lock the two parts of the structure together.

4. A neck brace comprising:
   at least one impact surface adjacent the neck of a wearer of the brace and facing generally upwardly, such that it is spaced from a helmet when the neck brace is worn with a helmet, said impact surface being configured to limit movement of the helmet by contacting an underside of the helmet;
   at least one bearing surface which is shaped and configured to bear on the wearer's body;
   a structure that extends between the impact surface and the bearing surface, said structure being sufficiently resilient to transfer impact loads from the helmet on the impact surface, to the wearer's body via the bearing surface; and
   restraining means in the form of at least one elongate flexible element that is attachable to the rear of the structure and to the helmet, wherein the elongate flexible element is releasably attachable to the structure immediately behind the wearer's neck at a level corresponding to an upper end of a thoracic spine and to the outside of the helmet in at least two spaced, lateral locations on either side of the helmet;
   wherein the structure includes at least two parts and at least one releasable clip mechanism configured to attach the parts of the structure to one another, said clip mechanism including:
   i. a protuberance defined on a first of the at least two parts of the structure;
   ii. a recess that is complementally shaped to the protuberance, defined on a second of the at least two parts of the structure, the protuberance and recess being shaped to allow pivotal movement between the protuberance and recess, relative to an axis within the clip mechanism, when the protuberance is received in the recess; and
   iii. a spigot about which the second part of the structure can pivot relative to the first part, when the protuberance is received in the recess, wherein said axis within the clip mechanism about which the protuberance and recess can pivot relative to each other when the protuberance is received inside the recess, is the axis of the spigot.

5. The neck brace of claim 4, wherein the restraining means is attachable to the structure by means of a releasable clip mechanism.

6. The neck braces of claim 4 or claim 5, wherein the restraining means includes an elongate element that extends between the spaced locations.

7. The neck brace of claim 6, wherein the restraining means includes an anchor element attachable to the structure and that defines an aperture, the elongate element passing through the aperture with clearance such that the elongate element has a general V-shape, between its spaced lateral attachments to the helmet and the anchor element.

8. The neck brace of claim 4, wherein the neck brace includes at least one lateral protuberance extending from the structure and being configured to extend along the body of the wearer underneath a body restraint.

9. The neck brace of claim 8, wherein each protuberance defines a generally planar surface on which an elongate element of the body restraint is receivable.

10. The neck brace of claim 8, wherein each protuberance includes an upstanding end, remote from the structure.

11. The neck brace of claim 4, wherein the structure is generally rigid.

12. The neck brace of claim 4, wherein the neck brace includes a flange extending from the structure, said impact surface being defined on the upper surface of the flange.

13. The neck brace of claim 4, wherein the neck brace includes at least one upstanding protuberance extending from the impact surface, said protuberance being configured to prevent the helmet of the wearer from sliding over the impact surface.

14. The neck brace of claim 4, wherein the neck brace includes a column that extends from the rear of the structure in a position corresponding with the upper spine of the wearer, said column being fixedly attached to the structure.

15. The neck brace of claim 4, wherein the structure is in the form of a ring that can extend around the wearer's neck.

16. The neck brace of claim 4, wherein the clip mechanism includes a detent that is configured to pivot about the axis of the spigot to draw the spigot closer to the first part of the structure, and to hold the two parts of the structure together and to hold the protuberance inside the recess.

17. The neck brace of claim 4, wherein the elongate flexible elements extend generally upright, when viewed from the side.

18. The neck brace of claim 4, wherein the elongate flexible elements extend substantially vertically when viewed from the side.

\* \* \* \* \*